United States Patent
Ohashi et al.

(10) Patent No.: US 7,186,880 B2
(45) Date of Patent: Mar. 6, 2007

(54) ADULT T CELL LEUKEMIA MODEL ANIMAL

(75) Inventors: Takashi Ohashi, Saitama (JP); Mari Kannagi, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 551 days.

(21) Appl. No.: 10/319,564

(22) Filed: Dec. 16, 2002

(65) Prior Publication Data

US 2003/0106079 A1    Jun. 5, 2003

Related U.S. Application Data

(63) Continuation of application No. 09/831,106, filed as application No. PCT/JP99/06175 on Nov. 5, 1999, now abandoned.

(30) Foreign Application Priority Data

Nov. 5, 1998    (JP) .............................. 10-315174

(51) Int. Cl.
  *A01K 67/00*    (2006.01)
  *C12N 5/00*    (2006.01)
  *G01N 33/00*    (2006.01)

(52) U.S. Cl. ............................ 800/10; 435/325; 800/3

(58) Field of Classification Search .................... None
  See application file for complete search history.

(56) References Cited

U.S. PATENT DOCUMENTS 6,004,565 A * 12/1999 Chiba et al. ............. 424/278.1

OTHER PUBLICATIONS

Tateno M. et al., J. Exp. Med., vol. 159, p. 1105-1116, (1984).
Tateno M. et al., Hokkaido Igaku Zasshi, vol. 62(1), pp. 74-81, (1987).
Imada K. et al., Japan J. Cancer Research, vol. 87, pp. 887-892, (1996).
Yamaoka S. et al., Oncogene, vol. 7, pp. 433-437, (1992).
Imada K. et al., Blood, vol. 86(6), pp. 2350-2357, (1995).
Stewart S.A. et al., Virology, vol. 226, pp. 167-175, (1996).
Tateno et al., "Rat Lymphoid Cell Lines with Human T Cell Leukemia Virus Production", J. Exp. Med., vol. 159, pp. 1105-1116, (1984).
Ohashi et al., "Induction of Adult T-Cell Leukemia-Like Lymphoproliferative disease and its Inhibition by Adoptive Immunotherapy in T-Cell-Deficient Nude Rats Inoculated with Syngeneic . . . ", Journal of Virology, pp. 6031-6040, (1999).

* cited by examiner

*Primary Examiner*—Celine Qian
(74) *Attorney, Agent, or Firm*—Wenderoth, Lind & Ponack, L.L.P.

(57) ABSTRACT

The present invention provides an adult T cell leukemia model animal, which is a T cell function deficient animal to which a cell line infected with human T cell leukemia virus-1 is transplanted. This model animal allows the HTLV-1 infected cell line to proliferate over a long period of time, and enables not only the tumorigenesis process but also the mechanism of onset of ATL and immune response mechanism of the host against ATL to be precisely analyzed.

3 Claims, 4 Drawing Sheets

ADULT T CELL LEUKEMIA MODEL ANIMAL

This application is a continuation of Ser. No. 09/831,106, filed Jun. 19, 2001, now abandoned, which is a U.S. national stage of International Application No. PCT/JP99/06175, filed Nov. 5, 1999.

TECHNICAL FIELD

The present invention relates to an adult T cell leukemia model animal. More particularly, the present invention relates to an adult T cell leukemia model animal that allows human T cell leukemia virus 1 to be proliferated for a long period of time, and allows detailed analysis of tumorigenesis process as well as tumorigenesis mechanism of adult T cell leukemia and immune response mechanisms of infected patients against leukemia.

TECHNICAL FIELD

Adult T cell leukemia (ATL) is a tumor of T cells induced by infection with human T cell leukemia virus-1 (HTLV-1).

Many mechanisms from infection of HTLV-1 to tumorigenesis, and development of disease conditions have not known yet. For example, no specific base sequences that characterize individual disease conditions have been found even by comparing viral base sequences in a variety of disease groups. Consequently, it has been supposed that the primary factor for determining various disease conditions in ATL is ascribed to factors of the infected patient (host).

Since the disease conditions in ATL range from acute to chronic syndromes with mild to acute progress, it is suggested that onset of ATL involves several steps. The multistep development of the disease in HTLV-1 infection is conjectured to be affected not only by the effect of spontaneously occurring mutation but also by the interaction between proliferation ability of the virus infected cells and immune response of the host against the virus.

Since the factors in host is strongly related to onset of ATL by HTLV-1 infection, a proper animal model is essential for solving the onset mechanism of ATL while effectively developing preventive, diagnostic and therapeutic methods.

The HTLV-1 infected cells using cultured cells have been established in ape, feline, rat and rabbit lymphocytes (Int. J. Cancer, 38:867–875, 1986; Int. J. Cancer 34:513–517, 1984; Jpn. J. Cancer Res., 76:86–94, 1985). HTLV-1 is also known to infect rabbit, ape and rat (Jpn. J. Cancer res., 76:86–94, 1985; Lab. Invest., 69:336–339, 1993; Int. J. Cancer, 40:403–407, 1987; J. Vilol., 66:6686–6694, 1992). Several animal models have been established using these sensitive animals for investigating the diseases related to HTLV-1. For example, a disease model animal using a WKA rat strain is often used for investigating pathological mechanisms of HAM/TSP related diseases (J. Exp. Med., 176:981–989, 1992; J. Vilol., 68:7221–7226, 1994).

While only a few examples of animal strains using rabbit and rat have been known as the ATL animal model, on the other hand, the application range thereof is limited. For example, although adult animals in the rabbit ATL model develop ATL like diseases with good reproducibility (Lab. Invest., 74:696–710, 1996), no immunological studies have been carried out in this animal model, mainly because inbred strains of rabbit can be hardly obtained. Since the ATL like disease are only observed in the neonatal rat ATL onset model with very short period of the disease duration, it is difficult to simultaneously perform oncological and immunological studies. It is also impossible to meet pathological versatility in ATL (J. Vilol., 66:6686–6694, 1992).

Although establishment of animal models are inevitable for solving the ATL onset mechanism and effectively developing preventive, diagnostic and therapeutic methods for the disease, the conventional animal models have not been satisfactory with respect to their diversely limited application ranges.

The present invention carried out by taking the foregoing problems into consideration and the object is to provide novel ATL animal models that can develop the ATL like diseases with good reproducibility over a long duration time besides permitting oncological and immunological studies.

DISCLOSURE OF INVENTION

The present invention for solving the foregoing problems provides an ATL model animal, which is a T cell function deficient animal transplanted with a HTLV-1 infected cell line. The HTLV-1 infected cell line is preferably derived from T cells of an animal having normal immunity, syngeneic to the T cell function deficient animal. It is also preferable that the T cell function deficient animal is a nude rat.

The present invention also provides a T cell line FPM1 established by infecting T cells of rat F344/N Jcl-rnu/+ having normal immunity with human T cell leukemia virus-1, and a T cell line FPM1-V1AX established by proliferating the cell line FPM1 in the body of a nude rat F344/N Jcl-rnu/rnu.

BEST MODE FOR CARRYING OUT THE INVENTION

Figure 1:
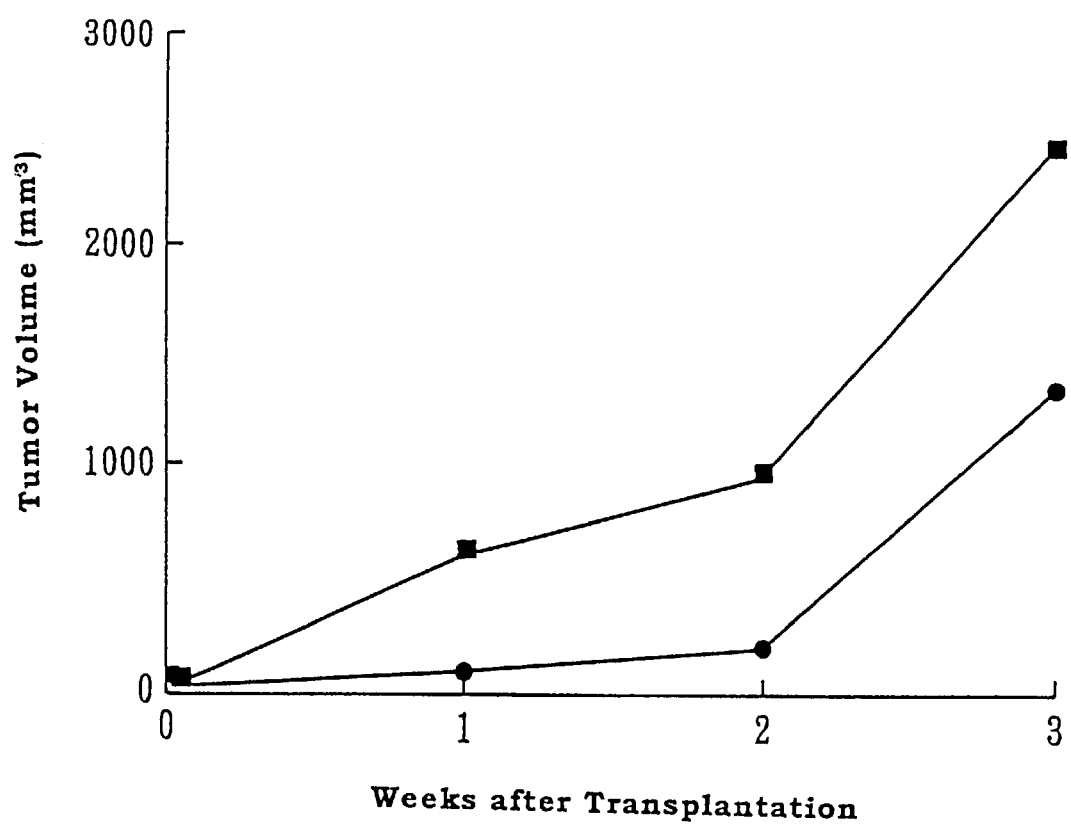
FIG. 1 is a graph showing subcutaneous proliferation of the cell lines F344-S1 (■) and TARS-1 (●).

The ATL model animal according to the present invention corresponds to an individual animal established by transplanting a HTLV-1 infected cell line into a T cell function deficient animal.

Rats and mice in which syngeneic animal strains have been established may be used as the objects for the T cell function deficient animal, including the existing nude rats and nude mice. The animals may be artificially created by knocking-out specific genes related to the T cell function. In the case of the T cell function deficient animal being thus artificially created one, wild-type animals thereof may be used as animals having normal immunity.

An already established existing cell line may be used for the HTLV-1 infected cell line, or the cell line may be independently established by infecting the animal cells with HTLV-1. In vitro or in vivo infection of the animal cells with HTLV-1 is also possible. When the animal cells are infected in vitro, thymus cells of the animal are cultivated together with the animal cells infected with HTLV-1.

The HTLV-1 infected T cell line FPM1 is a novel HTLV-1 infected cell line established by allowing the T cells of rat F344/N Jcl-rnu/+ having normal immunity to be infected with the human T cell leukemia virus-1.

The HTLV-1 infected cell line obtained as described above may be transplanted into the T cell function deficient animal, and may be subjected to proliferation/subculture in the animal body. The T cell line FPM1-V1AX according to the present invention is a novel HTLV-1 infected cell line established by proliferating the T cell line FPM1 in body of the nude rat F344/N Jcl-rnu/rnu.

Then, the HTLV-1 infected cell line is subjected to subcutaneous, intraperitoneal or intravenous transplantation into the T cell function deficient animals. The T cell function deficient animal may be an adult or a neonata (for example within 24 hours after the birth). The number of transplanted cells may be adjusted to $10^4$ to $10^8$ cells depending on the species and weight of the animal to be transplanted.

The animal transplanted with the HTLV-1 infected T cell line can proliferate the HTLV-1 infected T cell line for a long period of time, and continues to produce HTLV-1 products. Accordingly, it becomes possible to precisely analyze the tumorigenesis process as well as tumorigenesis mechanism of ATL and immunological response mechanism of the host against the tumor.

While the present invention is described in more detail with reference to the Examples, the present invention is by no means restricted to the Examples as set forth below.

EXAMPLE 1

Transplantation of HTLV-1 Infected Cell Line

Various existing HTLV-1 infected cell lines ($2 \times 10^6$ cells) were subcutaneously or intraperitoneally transplanted into neonatal rats (within 24 hours after the birth). The same cell lines ($10 \times 10^7$) were also subcutaneously, intraperitoneally or intravenously transplanted into the rats of age four week.

The HTLV-1 infected cell lines used were a lymphocyte cell line TARS-1 and TART-1 derived from WKA rats (J. Exp. Med., 176:981–989, 1992), a lymphocyte cell line F344-S1 derived from F344 rats (J. Exp. Med., 159:1105–1116, 1984), a HTLV-1 infected cell line W7TM-1 derived from WKA rats (J. Immunol., 144:4202–4211, 1990), and a HTLV-1 infected human cell line MT2 (Nature, 294:770–771, 1981).

The rats used were female F344/N Jcl-rnu/rnu nude rats (nu/nu) and F344/N Jcl-rnu/+ (nu/+) rats belonging to the same strain as the rats above (both of which were purchased from Clea Japan Co.), and female F344/Slc (F344) rats and WKA/KinSlc (WKA) rats (both of which were purchased from SLC Japan Co.).

The cell line transplanted animals prepared as described above were subjected to the following tests.

Procedures (1) Measurements of Subcutaneously Transplanted Cell Line

After the transplantation, the largest surface lengths of the subcutaneous cancer (a, mm) and width (b, mm) were measured once a week, and the dimension of the cancer was calculated by the following equation (Cancer Immunol. Immunother., 44:204–210, 1997).

$$V = a \times b^2 \times \frac{1}{2}$$

(2) Histological Tests of the Cell Lined Transplanted Animal

Ten week after the transplantation, organs of the animal were sampled and were observed under a microscope. After fixing the organs with formalin and embedding in paraffin, sliced specimens were stained with hematoxylin-eosin for microscopic observation. The frozen slice was immunohistologically stained using primary antibodies such as a monoclonal antibody against an anti-rat IL-2 receptor α-chain, anti-rat CD4 mAb or an anti-HTLV-1 Tax mAb (LT-4) (Jan. J. Cancer Res., 81:225–231, 1990).

(3) Detection of HTLV-1 Provirus

Genomic DNAs were isolated from the organs of the transplanted animal, and the px region of the HTLV-1 provirus was amplified by PCR following the method described in the literature (J. Vilol., 72:7289–7293, 1998). The genome was also subjected to reverse PCR to specify the chain sequence of 3'-terminus side of provirus following the method described in the literature (Blood, 84:3080–3085, 1994).

Sequences of PCR products were determined using a commercially available sequencer.

Results:

(1) In vivo Proliferation of HTLV-1 Infected Cells

Table 1 shows the results of microscopic observations of the HTLV-1 infected cell line, rats transplanted with the cell line, transplantation pathway and each organ.

As shown in Table 1, the cell lines F344-S1 and TARS-1 generally proliferated in the nude rat (nu/nu) irrespective of the transplantation pathway. FIG. 1 shows the graph showing the subcutaneous proliferation of the cell lines F344-S1 (■) and TARS-1 (●).

Of the five rats transplanted with F344-S1, three died three week after transplantation. The remaining four were allowed to commit euthanasia 3, 4, 7 and 8 weeks after transplantation since they were extremely debilitated. One of these rats developed dysbasia, and others expressed severe jaundice. The rats transplanted with the cell line TARS-1 survived, on the other hand, 10 week after transplantation.

The results of autopsy revealed that the degree of proliferation of the transplanted cells was the largest in the nude rat lacking the T cell function. However, the cell lines F344-S1 and TARS-1 did not proliferate in the rat of normal immunity. As shown in Table 1, TART-1, W7TM-1 and MT-2 did not proliferate in the nude rat as well as in the animals of normal immunity.

TABLE 1

| cell line | crigin | recipient | number | root | diagnosis[a] |
|---|---|---|---|---|---|
| P344-S1 | F344 | F344 (NB[b]) | 4 | ip[c] | NS[d] |
| | | F344 (4W) | 2 | sc[e] | NS |
| | | nu/nu (4W) | 5 | sc | multiple progressive subcutaneous tumor with metastasis |
| | | nu/nu (4W) | 1 | ip | multiple progressive intraperitoneal tumor |
| | | nu/nu (4W) | 1 | iv[f] | multiple progressive systemic tumor |
| TAR-S1 | WKAH | WKAH (4W) | 5 | sc | transient subcutaneous tumor (1 w[g]) |
| | | WKAH (4W) | 1 | ip | NS |
| | | nu/nu (4W) | 3 | sc | progressive subcutaneous tumor with metastasis to |

TABLE 1-continued

| cell line | crigin | recipient | number | root | diagnosis[a] |
|---|---|---|---|---|---|
| | | nu/nu (4W) | 1 | ip | lung multiple progressive intraperitoneal tumor |
| | | nu/nu (4W) | 1 | iv | multiple progressive systemic tumor |
| TART-1 | WKAH | WKAH (NB) | 9 | sc | NS |
| | | nu/nu (4W) | 1 | sc | NS |
| W7TM-1 | WKAH | WKAH (4W) | 7 | sc | NS |
| | | nu/nu (4W) | 1 | sc | NS |
| MT-2 | human | nu/+ (4W) | 4 | iv | NS |
| | | nu/nu (4W) | 4 | iv | NS |
| | | F344 (4W) | 4 | ip | NS |

[a]autopsy four or ten week after transplantation
[b]newborn
[c]intraperitoneal transplantation
[d]no syndrome
[e]subcutaneous transplantation
[f]intravenous transplantation
[g]Proliferation of tumor cells were observed in first week after transplantation.

(2) Tumor Metastasis in Adult Nude Rat

Nodes of tumor were observed in the lung, liver, spleen, spinal code, ovary and lymph node from the results of autopsy of the rats transplanted with the F344-S1 cell line. Histological inspection showed large infiltration of the tumor cells in the lung, lymph node and subcutaneous layer. No metastasis of the tumor was observed, on the other hand, in the rats transplanted with TARS-1, except one rat that showed metastasis to the lung.

(3) Distribution of Provirus HTLV-1 in the Tissue

Table 2 shows the results of analysis in which distribution of the provirus in the tissue of the nude rat transplanted with the cell lines F344-S1 and TARS-1 was analyzed by PCR. It is clear from Table 2 that HTLV-1 proviral DNA was detected in almost all the inspected tissues in all the rats transplanted with F344-S1. The proviral DNA was also detected in almost all the tissues inspected, although it was not found in all the rats transplanted with TARS-1. It was confirmed from the results in (2) that HTLV-1 has been distributed in the tissues in which apparent metastasis has not been apparent.

cin; 10 U/ml of interleukin 2 was added at initiation of culture) to establish the HTLV-1 infected T cell line FPM1. This cell line FPM1 expresses CD4, CD5, CD25, MHC-1 and MHC-II as the cells of the human ATL patient do.

The established HTLV-1 infected T cell line FPM-1 was cultivated in a RPMI1640 medium (containing 10% FCS and antibiotics).

The cell line FPM1 ($1 \times 10^7$ cells) was subcutaneously transplanted in the 4-week-old rats. The cell line FPM1 ($2 \times 10^6$ cells) was also subcutaneously a transplanted in neonatal rats (within 24 hours after the birth).

While growth of the subcutaneous tumor was observed in two week after the first transplantation in the 4-week old nude rat received subcutaneous transplantation of FPM1, the cancer was gradually shrunk and finally disappeared. No evident metastasis was also observed. However, since HTLV-1 proviral DNA was detected in many tissues by PCR using the genomic DNA of each tissue as a template as shown in Table 2, it was confirmed that the cell line FPM1 was transferred into various tissues even when apparent metastasis had not been observed.

Increase of tumors was also observed, on the other hand, for a period of two weeks in the neonatal nude rats transplanted with FPM1. The rats were allowed to commit euthanasia thereafter since they were extremely debilitated. The immunohistological inspection revealed that infiltrating tumor cells evidently expresses IL-2 receptor. The rat CD4 and HTLV-1 tax were also slightly positive in these tumor cells. No tumor cells were observed at all in the neonate rat of normal immunity transplanted with FPM1.

EXAMPLE 3

Establishment of HTLV-1 Infected T Cell Line FPM1-V1AX and Transplantation into Rat FPM1 cells proliferated in the natal nude rat were isolated to establish the cell line FPM1-N2. The cell line was then subcutaneously transplanted into the natal nude rat (nu/nu) and the syngeneic rat (nu/+) thereof having mormal immu-

TABLE 2

| cell line | cerebrum | cerebellum | submamndibular gland | heart | lung | liver | spleen | kidney | spinal cord | bone marrow | peripheral blood |
|---|---|---|---|---|---|---|---|---|---|---|---|
| F344-S1 | 3/3 | 3/3 | 2/3 | 3/3 | 3/3 | 3/3 | 3/3 | 3/3 | 3/3 | 3/3 | 3/3 |
| TRS-1 | 0/3 | 1/3 | 1/3 | 2/3 | 3/3 | 3/3 | 1/3 | 1/3 | 2/3 | 3/3 | 2/3 |
| FPM1 | 0/3 | 3/3 | 0/3 | 0/3 | 2/3 | 1/3 | 3/3 | 2/3 | 2/3 | 0/3 | 0/3 |

*The DNAs purified from each tissue shouwn in the Table were amplified by PCR to 10 week after transplantation.
*From each cell line $10^7$ cells were transplanted in nu/nu rat.

EXAMPLE 2

Establishment of HTLV-1 Infected T Cell Line FPM1 and Transplantation thereof into Rat Spleen cells of rat F344/N Jcl-rnu/+nu/+ were cultivated together with HTLV-1 infected human cell line MT-2 in a RPMI1640 medium (containing FCS, penicillin, streptomynity. Although the transplanted cells did not proliferate in the rats of normal immunity (five rats), the transplanted cells proliferated in the four nude rats. Three of these rats died two week after the transplantation, and the remaining one was allowed to commit euthanasia. Thickening of the lymph node was observed by autopsy. The thickened cells were isolated, and were cultivated to establish the cell line FPM1-V1AX. The results are shown in Table 3.

TABLE 3

| cell line | origin | recipient | number | root | diagnosis[a] |
|---|---|---|---|---|---|
| FMP1 | in vitro transformation | nu/+ (NB[b]) | 2 | sc[c] | NS[d] |
|  |  | nu/nu (NB) | 2 | sc | progressive tumor |
|  |  | nu/+ (NB) | 5 | ip[e] | NS |
|  |  | nu/nu (NB) | 3 | ip | death (2W[f]) |
|  |  | nu/nu (4W) | 4 | sc | transient tumor |
|  |  | nu/nu (4W) | 2 | ip | NS |
| FPM1-N2 | subcutaneous tumor | nu/+ (NB) | 5 | sc | NS |
|  |  | nu/nu (NB) | 4 | sc | progressive subcutaneous tumor with metastasis to lymph node |
| FPM1-V1AX | axilla lymph node | nu/nu (4W) | 4 | sc | multiple progressive subcutaneous tumor with systemic metastasis |

[a]autopsy four or ten week after transplantation
[b]newborn
[c]subcutaneous transplantation
[d]no syndrome
[e]intraperitoneal transplantation
[f]The rats died within two weeks after transplantation Subsequently, the cell line FPM1-V1AX was intraperitoneally transplanted into three adult nude rats, confirming that the tumor was grown in all the three rats. One of the three rats died two week after the transplantation, and the remaining two were allowed to commit euthanasia three weeks later. The results of autopsy showed metastasis of the tumor into the liver and thickening of the lymph node in all three rats. Metastasis into the kidney and spleen was also observed in one rat.

Figure 2:
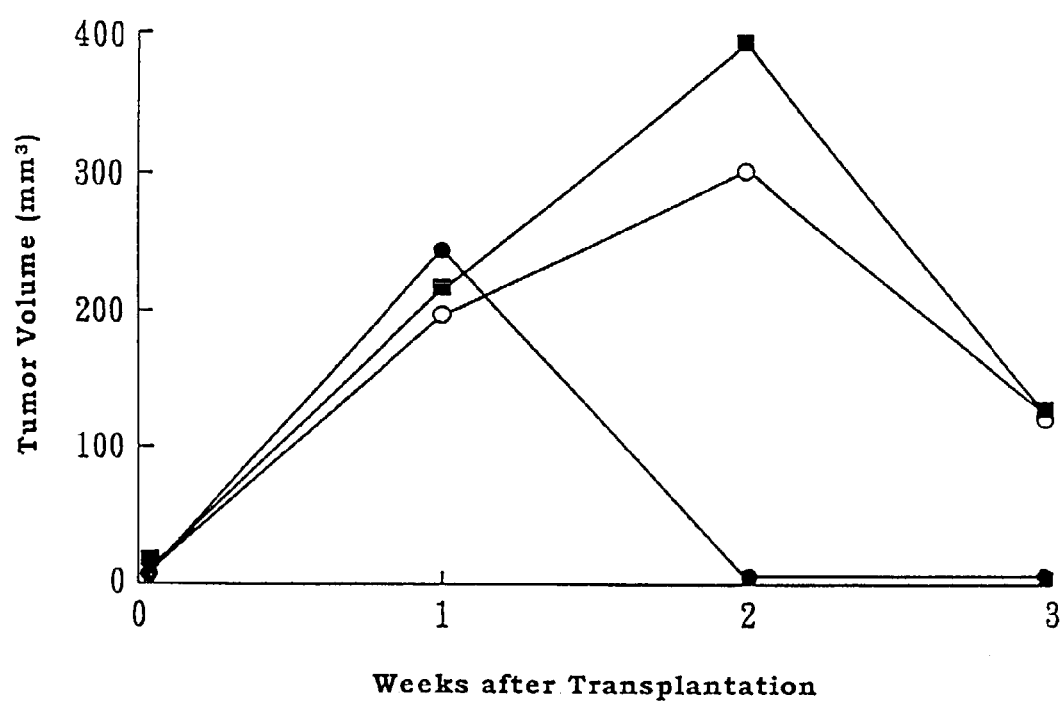
FIG. 2 is a graph showing the tumor growth process in animals transplanted with FPM1-V1AX alone (■), naive T cells and FPM1-V1AX (○), and immune T cells and FPM1-V1AX (●).

T cells of the rat of normal immunity (age four week) immunized with the FPM1 cell line established in Example 2 were intraperitoneally administered to the adult nude rats with simultaneous subcutaneous transplantation of FPM1-V1AX. The results are shown in FIG. 2. The subcutaneous tumor continued to grow until two week after the transplantation in the animals transplanted with FPM1-V1AX alone (■) and with naive T cells and FPM1-V1AX (○), the tumor contracted in the animal transplanted with the immune T cells and FPM1-V1AX (●). No metastasis of the tumor was observed in the animals in which the tumor contracted. In the control animals, on the other hand, metastasis of the tumor into the lung and liver was observed.

It was confirmed from these results that the T cell immune system is greatly involved for inhibiting proliferation of the tumor.

EXAMPLE 4

Induced T-ell Immunity by HTLV-1 Tax Gene

The HTLV-1 tax expression plasmid and control plasmid were administered to hetero-rats of normal immunity once a week for successive two weeks using a gene gun. T cells were isolated one week after the final administration. These T cells were stimulated with FPM1-V1AX for one week, followed by measurement of cytotoxic activity against FPM1-V1AX and FPM-SV.

Figure 3:
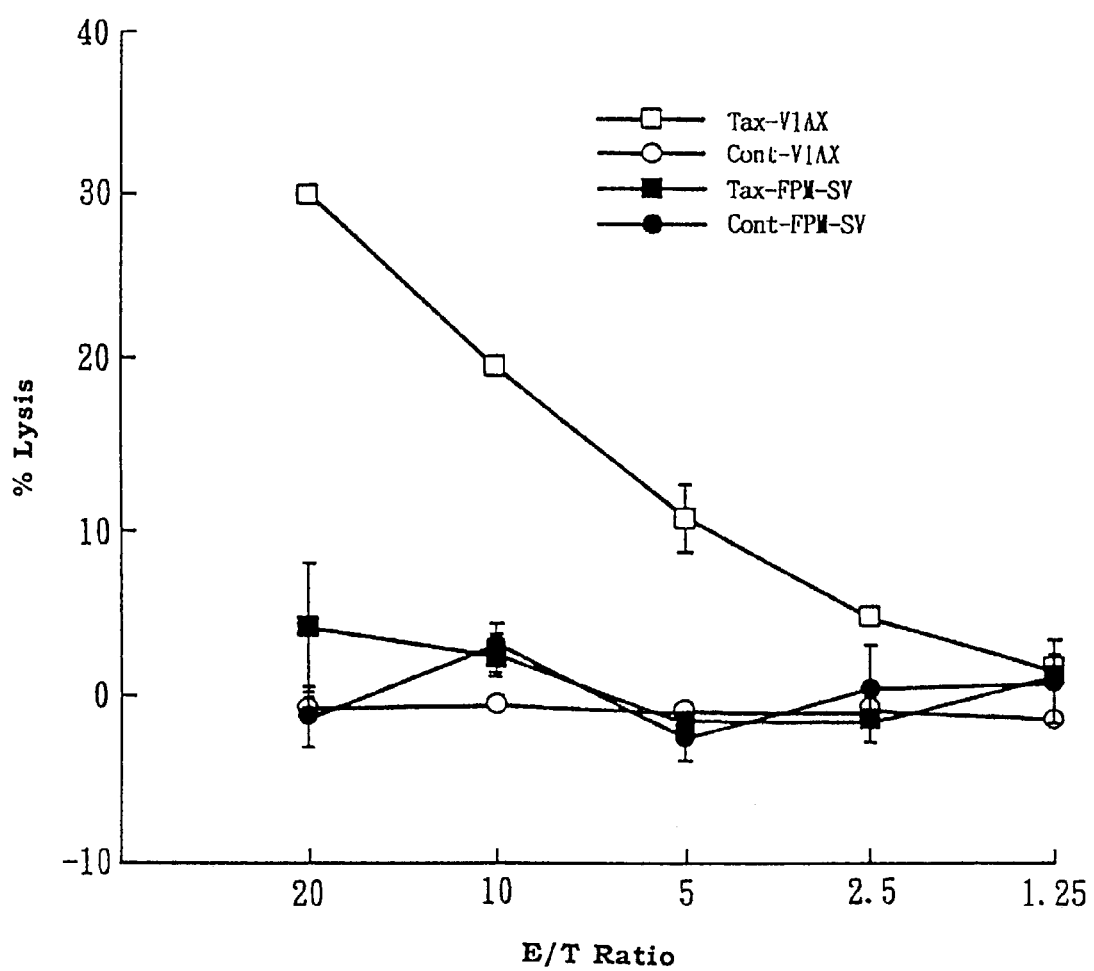
FIG. 3 is a graph showing a specific cytotoxic activity of the T cells from rat having normal immunity against the HTLV-1 infected T cells. Tha rat is subjected immune induction by using HTLV-1 tax gene.

The results are shown in FIG. 3. Only the T cells derived from the rats administered with the tax expression plasmid showed the cytotoxic activity specific to the HTLV-1 infected cells.

EXAMPLE 5

Effect of the Tax Immunized T Cells on the ATL Model Animal

FPM1-V1AX was subcutaneously transplanted into nude rats transplanted with T cells derived from the tax expression plasmid administered rats prepared in Example 4, and with T cells derived from control plasmid administered rats, respectively, and into nude rats not transpalnted with the T cells. The size of each subcutaneous cancer was measured for assessing growth of the tumor.

Figure 4:
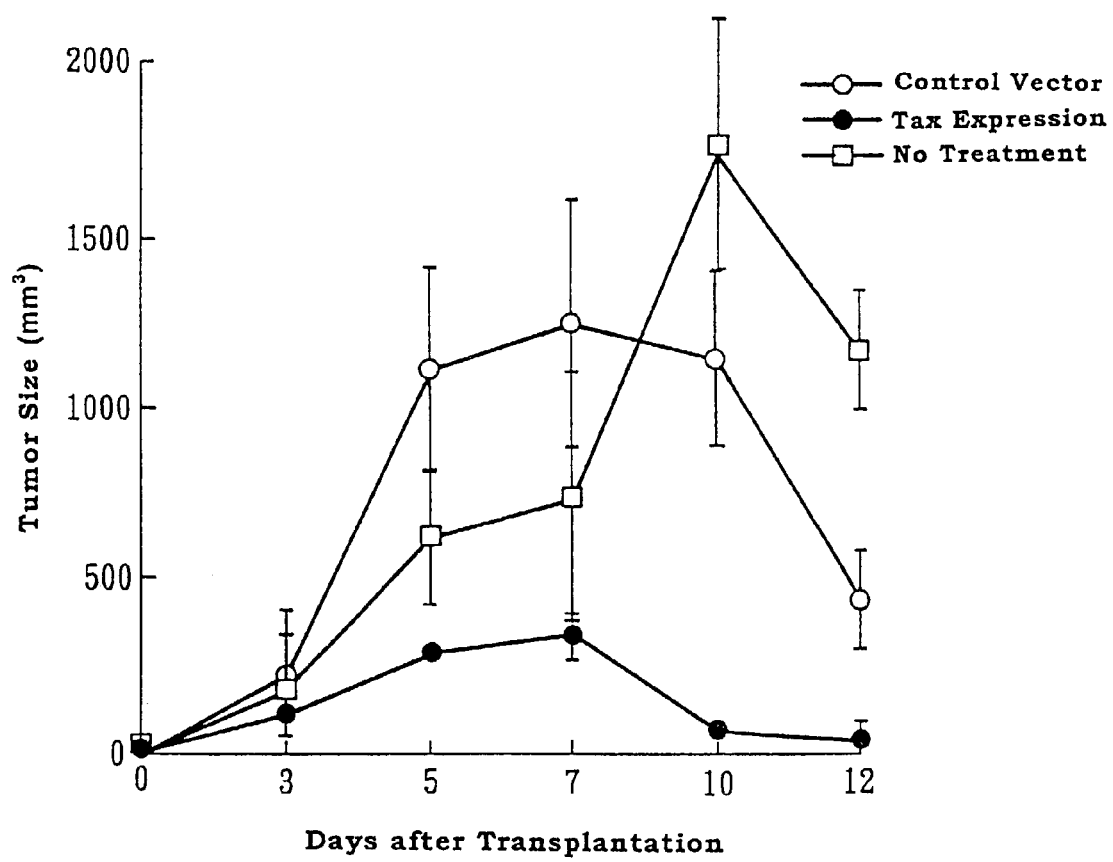
FIG. 4 is a graph showing effect of the tax immune T cells on the development of tumors in the ATL model animal.

The results are shown in FIG. 4. It was confirmed that the T cells derived from the rats administered with the tax expression plasmid strongly suppress in vivo proliferation of the HTLV-1 infected cells.

INDUSTRIAL APPLICABILITY

The present invention provides an ATL model animal that allows the HTLV-1 infected cell line to proliferate in vivo over a long period of time. This model animal enables not only the tumorigenesis process but also the mechanism of onset of ATL and immune response mechanism of the host against ATL to be precisely analyzed.

The invention claimed is:

1. An adult T cell leukemia model rat, which is a T cell function deficient nude rat F344/N Jcl-rnu/rnu, said model rat containing transplanted cells of cell line FPM1-V1AX, said cell line being infected with human T cell leukemia virus-1, said cell line being obtained from T cells of a syngeneic rat F344/N Jcl-rnu/+ having normal immunity, wherein said model rat develops tumors.

2. The adult T cell leukemia model rat according to claim 1, in which the tumors contract when treated with transplanted T cells obtained from a rat F344/N Jcl-mu/+ immunized with cells of cell line FPM1-V1AX.

3. A human T cell leukemia virus infected cell line FPM1-V1AX, which is obtained by:
   infecting T cells of rat F344/N Jcl-rnu/+ having normal immunity with human T cell leukemia virus-1,
   proliferating said T cells in a newborn nude rat F344/N Jcl-rnu/rnu, and
   isolating T cells from the rat which have the following characteristics:
   (a) the cells proliferate in a nude rat F344/N Jcl-rnu/rnu, but not in a rat F344/N Jcl-rnu/+, and
   (b) the cells grow into a tumor in an adult nude rat.

* * * * *